United States Patent
Thomas et al.

(10) Patent No.: US 11,307,118 B2
(45) Date of Patent: Apr. 19, 2022

(54) DYNAMIC ENVIRONMENTAL WATER SAMPLING BACKPACK

(71) Applicants: Austen Thomas, Vancouver, WA (US); Jesse Howard, Vancouver, WA (US); Lorin Mueller, Vancouver, WA (US); Mike Tavakoli, Vancouver, WA (US)

(72) Inventors: Austen Thomas, Vancouver, WA (US); Jesse Howard, Vancouver, WA (US); Lorin Mueller, Vancouver, WA (US); Mike Tavakoli, Vancouver, WA (US)

(73) Assignee: Smith-Root, Inc., Vancouver, WA (US)

( * ) Notice: Subject to any disclaimer, the term of this patent is extended or adjusted under 35 U.S.C. 154(b) by 505 days.

(21) Appl. No.: 15/678,964

(22) Filed: Aug. 16, 2017

(65) Prior Publication Data

US 2018/0052080 A1     Feb. 22, 2018

Related U.S. Application Data

(60) Provisional application No. 62/375,886, filed on Aug. 16, 2016.

(51) Int. Cl.
| | |
|---|---|
| *G01N 1/14* | (2006.01) |
| *A45F 3/04* | (2006.01) |
| *G01N 33/18* | (2006.01) |
| *G01N 1/10* | (2006.01) |

(52) U.S. Cl.
CPC ............... *G01N 1/14* (2013.01); *A45F 3/04* (2013.01); *G01N 33/18* (2013.01); *A45F 2003/045* (2013.01); *A45F 2200/05* (2013.01); *G01N 2001/1006* (2013.01); *G01N 2001/1056* (2013.01); *G01N 2001/1418* (2013.01)

(58) Field of Classification Search
USPC ............................................. 73/864.34
See application file for complete search history.

(56) References Cited

U.S. PATENT DOCUMENTS

| | | | | |
|---|---|---|---|---|
| 4,660,422 A | * | 4/1987 | Eads | G01N 1/14 700/282 |
| 4,942,770 A | * | 7/1990 | Seifert | C12M 33/00 73/864.34 |
| 5,167,802 A | * | 12/1992 | Sandstrom | G01N 1/18 137/565.3 |
| 5,339,700 A | * | 8/1994 | Wright | B01L 3/505 422/944 |
| 5,546,818 A | * | 8/1996 | Keefer | B01L 9/06 141/284 |
| 5,576,503 A | * | 11/1996 | Nabity | E21B 43/121 141/130 |
| 7,704,746 B1 | | 4/2010 | Curt et al. | |

(Continued)

*Primary Examiner* — Peter J Macchiarolo
*Assistant Examiner* — Mohammed E Keramet-Amircolai
(74) *Attorney, Agent, or Firm* — J. Curtis Edmondson; Law Office of J. Curtis Edmondson

(57) ABSTRACT

A dynamic device for sampling of a body of water, featuring the use of sterile collection equipment and precise parametric controls based on feedback data, so that when the device is activated the product of the sampling and filtration process therein accurately indicates the characteristics of the body of water from which the sample was taken. Various sensors help in providing data for bringing about precise parametric control of the dynamic device.

1 Claim, 10 Drawing Sheets

(56) References Cited

U.S. PATENT DOCUMENTS

| | | | |
|---|---|---|---|
| 2001/0037693 A1* | 11/2001 | Smith | G01N 1/14 73/864.34 |
| 2008/0030712 A1* | 2/2008 | Tokhtuev | G01N 21/6402 356/51 |
| 2010/0068821 A1 | 3/2010 | Randy et al. | |
| 2010/0170350 A1* | 7/2010 | Stevens | G01N 1/14 73/864.34 |
| 2010/0206096 A1* | 8/2010 | Lee | G01N 1/2211 73/864.34 |
| 2010/0283620 A1* | 11/2010 | Calio | G01N 1/2273 340/606 |
| 2011/0009019 A1* | 1/2011 | Neira | G01N 1/14 441/1 |
| 2012/0105830 A1 | 5/2012 | Pierce et al. | |
| 2014/0053663 A1* | 2/2014 | Roine | G01M 1/00 73/864.34 |
| 2014/0284465 A1 | 9/2014 | Potters et al. | |
| 2015/0007648 A1 | 1/2015 | Thoron et al. | |
| 2015/0177212 A1* | 6/2015 | Thomas | G01C 13/00 114/331 |
| 2015/0268136 A1* | 9/2015 | Detweiller | G01N 1/14 73/864.34 |
| 2016/0018558 A1* | 1/2016 | Bond | G01V 9/007 250/255 |

\* cited by examiner

800

DYNAMIC ENVIRONMENTAL WATER SAMPLING BACKPACK

CROSS REFERENCES TO RELATED APPLICATIONS

This application claims the benefit of U.S. Provisional Patent Application No. 62/375,886, filed Aug. 16, 2016, entitled as "Dynamic Environmental Water Sampling Backpack", which is incorporated herein by reference in its entirety.

BACKGROUND

The present inventive subject matter relates to the systems and methods for the analysis of aquatic environments using a backpack-mounted water sampling system.

Scientists frequently conduct research of the water column in order to characterize certain aquatic environments. The protocol for conducting such research normally includes the capture of water samples from the environment of interest, extraction of particulate from those samples, and analysis of the particulate in order to determine characteristics such as biological species present, molecular composition of particulate, etc. The quality of this environmental water analysis is a direct product of the quantity of water sampled, the proportion of particulate captured and preserved, and the effectiveness of measures taken to prevent introduction of contaminants to the sampling system.

The original protocol of sampling from target locations has involved manual collection of water samples in the field into containers and transport of the filled containers to remote laboratories for analysis. The quality of the analysis afforded by this protocol is limited by sample size, which is restricted to the amount of water that can be transported from the sampling location to the remote laboratory; sample quality, which can vary widely based on the technique used to collect the water sample; and the potential for introducing contaminants to the sample, either through water induction, exposure of contained samples to unclean environments, or impurities in the container itself. In addition, remote testing of samples at a laboratory is normally a very expensive and lengthy process. Subsequent advances in sampling protocol involved processing of water samples through a filtration device, either by direct feed from the intake point or by induction from a container through a filtration device via gravity feed, and packaging of the filters for transport to remote laboratories for analysis. These advances improved analysis by increasing the potential sample size, but did not improve potential sample quality, preclude the possibility of introducing contaminants to samples, or decrease cost or lead time of analysis conducted in remote laboratories.

Field-based pump and filter systems have previously been developed for sampling aquatic environments. A water sampling device attached to a buoy is the subject of U.S. Pub. No. 20160018558, and an aerial water system is the subject of U.S. Pub. No. 20150268136.

As is clear from the prior art, there is a considerable body of work associated with the processing of water through a filtration and particulate collection system after a water sample has been inducted and before the filter has been removed from the system for analysis. However, other measures to improve the quality and representativeness (i.e., the capture of an accurate representation of the water) of samples by automatically or manually controlling the flow rate, pressure, and total volume of water flowing through the intake point during water sampling evolutions; preventing the introduction of contaminants to the sampling system throughout the intake and analysis process; and facilitating field-based aquatic environmental analysis have not been contemplated by the prior art.

SUMMARY

The present inventive subject matter overcomes problems in the prior art by providing systems and methods for an apparatus to take a particulate sample from a body of water, said apparatus having an optional-use sterile induction tube; a disposable filter assembly; an electric flow sensor; a remote pump controller with a feedback display; a backpack-based apparatus containing a protective casing, storage compartments, a positive displacement pump, a battery, a user interface panel, an electric pressure sensor, a display screen, pump tubing, a pump system controller, a pump driver, an onboard computer, and a discharge container; and a sterile supplies pouch.

The optional-use sterile induction tube wherein water can be drawn from the body of water and directed to the filter assembly.

The disposable filter assembly wherein a sterile filter membrane collects particulate from the water sample and holds it for subsequent analysis.

The electronic flow sensor wherein digital information related to the volume of water flowing through the induction and filtration system is collected and communicated to the remote flow controller.

The remote flow controller wherein flow rate and volume are calculated using data received from the electronic flow sensor, total volume is displayed to the user for monitoring purposes, digital information related to flow rate and volume is transmitted to the pump system controller for control purposes, and manual directions can be entered by the user.

The backpack-based device wherein maximum parameters for flow rate, pressure, and volume can be set by the user; a pump generates a vacuum to draw water into the system; feedback for actual performance can be received from the various controllers computing useful information from sensory data; and pump speed can be automatically controlled based on the comparison of feedback and parameter data.

The sterile supplies pouch wherein air-tight protection from contamination is provided to the filter membrane, filter housing, induction tube and forceps to ensure accurate water sampling.

The foregoing is not intended to be an exhaustive list of embodiments and features of the present inventive subject matter. Persons skilled in the art are capable of appreciating other embodiments and features from the following detailed description in conjunction with the drawings.

DETAILED DESCRIPTION

Figure 1:
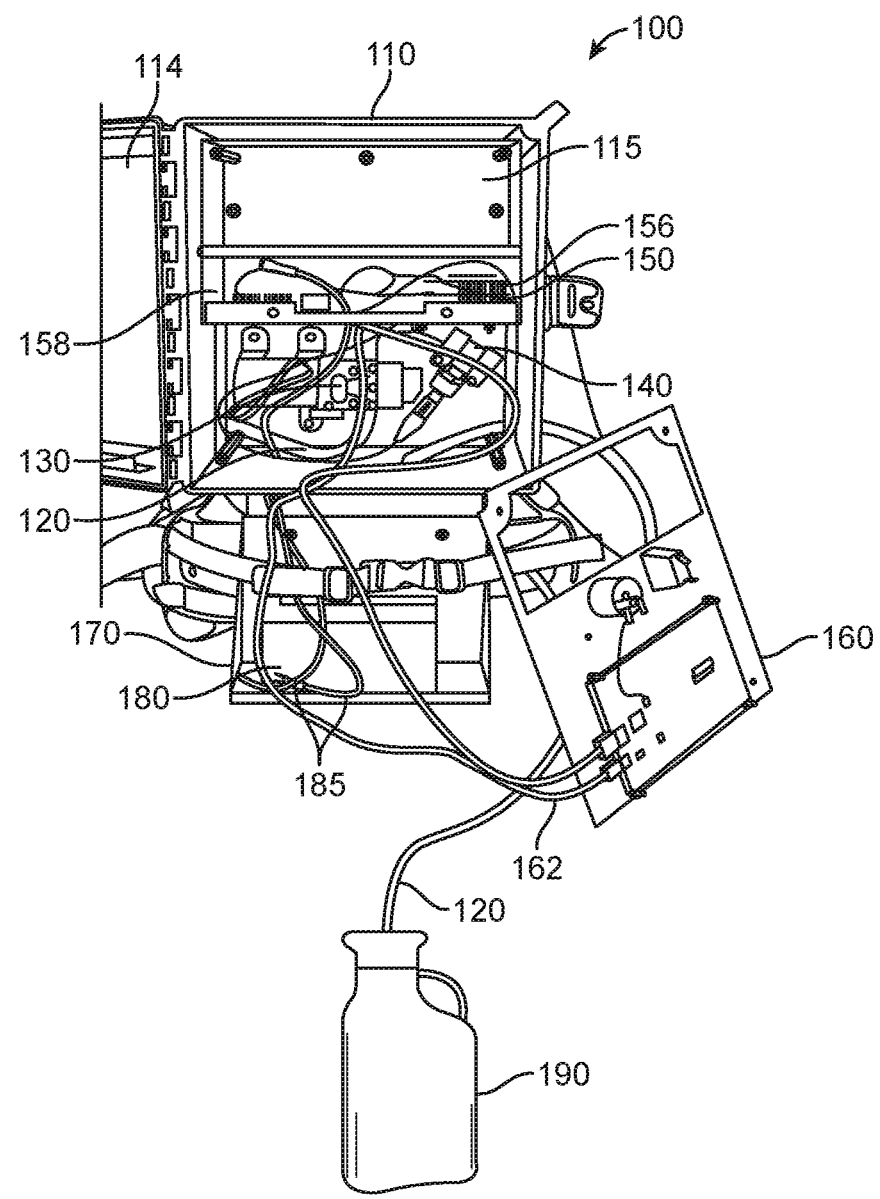
FIG. 1 is a front view diagram of the power and control module.

Representative embodiments according to the inventive subject matter are shown in FIGS. 1-10 wherein similar features share common reference numerals.

Now referring to FIG. 1 which depicts the inventive subject matter of the power and control module 100 consisting of the controller casing 110, the protective lid 114, the storage compartment 115, the pump tubing 120, the water pump 130, the pressure sensor 140, the pump system controller 150, the pump driver 156, the onboard computer 158, the user interface panel 160, the touch screen output wire 162, the battery compartment 170, the battery 180, the battery wires 185, and the discharge container 190. The power and control module 100 is attached to backpack-style harnessing to make the system portable in a variety of environments. The controller casing 110 and the protective lid 114 protect the water pump 130, the pressure sensor 140, the user interface panel 160, and the contents of the storage compartment 115 from shock impact and environmental contamination. The storage compartment 115 provides storage space for storage of preserved filter membranes, storage media for field data collection, pens/pencils for sample labeling, and sample containers. The pump tubing 120 directs the flow of water throughout the entire sampling system. The water pump 130 is a variable-speed pump used to create a desirable level of vacuum within the pump tubing 120 that enables the collection of the water sample and its movement through the water sampling process. Water entering the power and control module through the pump tubing 120 is directed to a pressure sensor 140, which collects digital information related to water pressure and transmits it to the pump system controller 150. The pump system controller 150 receives data from a variety of sensors, computes system performance against parameters that are preset by the user, and sends digital information based on those computations to the pump driver 156 and the onboard computer 158. The pump driver 156 receives digital information generated by the pump system controller 150 and executes orders that adjust the operating speed of the water pump 130. The onboard computer 158 receives digital information generated by the pump system controller 150 and transmits it via a wired connection to the interface Panel 160, the touch screen output wire 162 is then used to send user input from the user interface panel 160 back to the onboard computer 158. The user interface panel 160 contains a display screen that displays water flow rate, pressure, and volume metrics for the current water sample and enables the user to set parameters for said metrics. Water exiting the water sample collection system subsequent to flowing through the sampling process is discharged via the pump tubing 120 and collected in the discharge container 190 to prevent reentry to and contamination of the water undergoing sampling.

Figure 2:
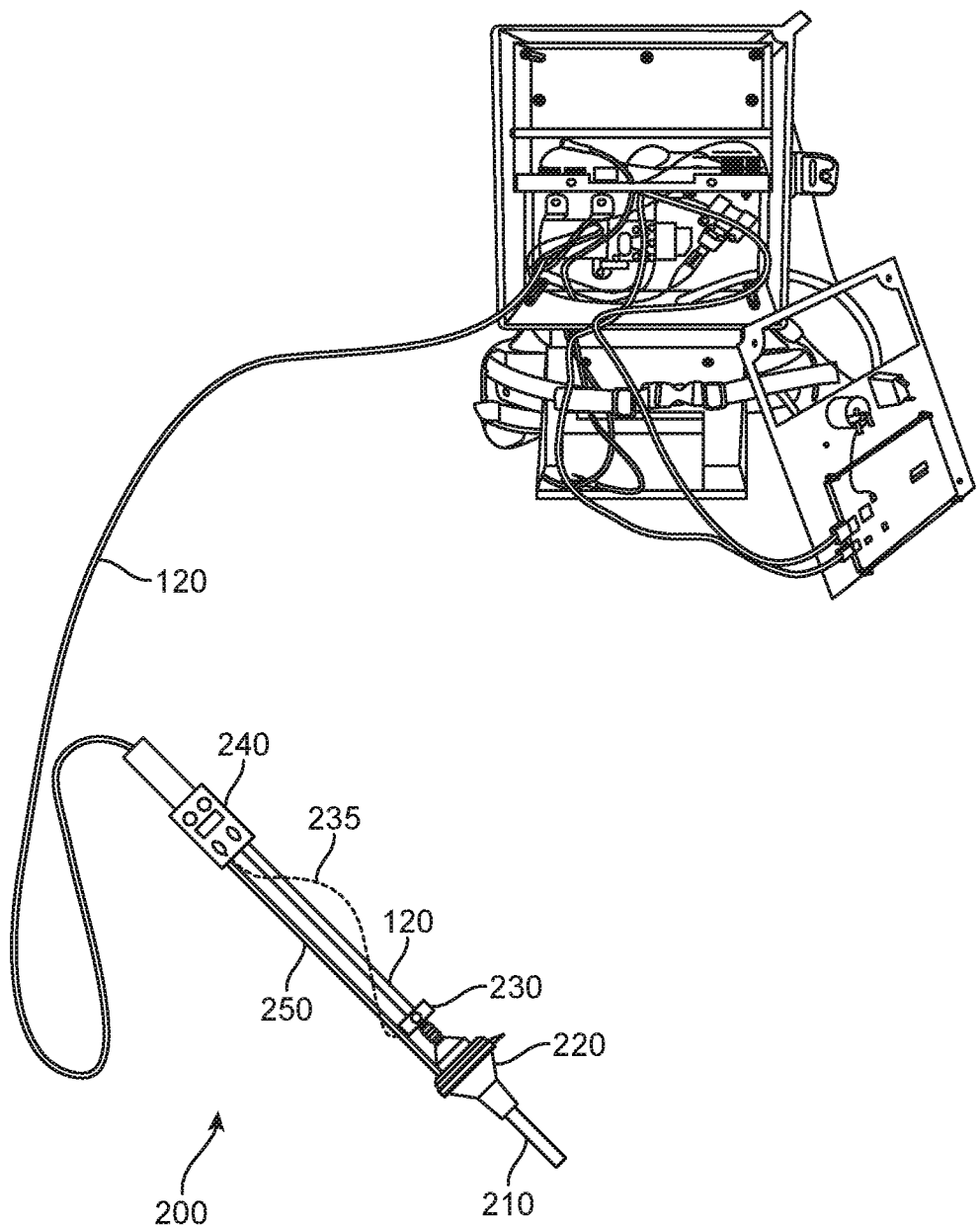
FIG. 2 is a top view diagram of the water collection and filtration module.

Now referring to FIG. 2 which depicts the inventive subject matter of the water collection and filtration module 200, consisting of the induction tube 210, the filter assembly 220, the pump tubing 120, the flow rate sensor 230, the flow sensor wires 235, the remote flow controller 240, and the wand extension 250. In some embodiments, the flow rate sensor 230 may be located inside the casing for power and control module 100. The induction tube 210 draws water from the sampling source, using the vacuum generated by the pump, and directs the water into the filter assembly 220. Water flows through the filter assembly 220, where particulate is captured, and then flows into the pump tubing 120, at which point the flow rate sensor 230 collects water flow rate data and transmits digital information via the flow sensor wires 235 to the remote flow controller 240. The remote flow controller 240 contains toggle switches that enable operation in manual or automated mode, buttons enabling the user to manually start and stop operation of the pump, and a display screen to enable the user to monitor volume. Water flow rate information fed to the remote flow controller 240 from the flow rate sensor 230 is transmitted wirelessly to the pump system controller to facilitate the control of water flow. The telescoping wand extension 250 provides necessary rigidity through its attachment to the filter assembly 220, the pump tubing 120, the flow rate sensor 230, the remote flow controller 240, and the wand extension 250. The wand extension 250 is retractable and includes an integrated tripod stand to facilitate draining of the filter assembly 220 subsequent to water sampling. Users can control the positioning of the water collection and filtration module by gripping a plastic handle joining the underside of the remote flow controller 240 with the wand extension 250.

Figure 3:
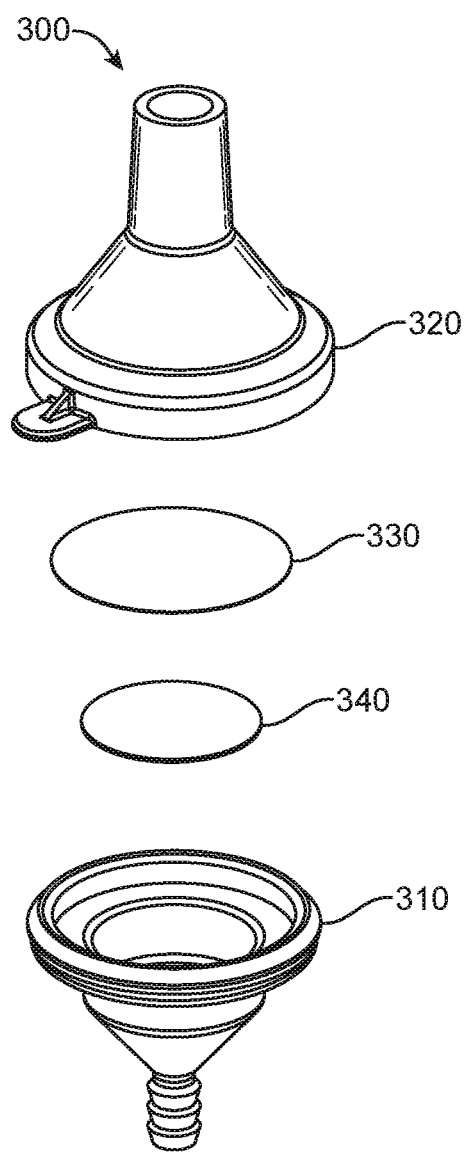
FIG. 3 is an exploded view diagram of the filter assembly.

Now referring to FIG. 3 which depicts the inventive subject matter of the filter assembly 300, consisting of the lower filter housing 310, the upper filter housing 320, the filter membrane 330, and the filter screen 340.

The lower filter housing 310 is made of a hard polymer that provides rigidity and enables it to form a water-tight seal when its male connector end is inserted into the pump tubing 120. The upper filter housing 320 is made from a stiff rubber-like material that enables it to form water-tight seal at its base when fitted over the lower filter housing 310 and at its female connector end when fitted over the end of the optional-use induction tube 210. The upper filter housing 320 also contains a pull-type tab along the exterior ridge of its base to facilitate its removal from the lower filter housing 310. The lower filter housing 310 and upper filter housing 320, when joined, contain and protect from contamination the filter membrane 330 and the filter screen 340. The filter membrane 330 captures particulate as water flows through the filter assembly 300, and is removable for subsequent analysis of the captured particulate. The filter screen 340, permanently mounted in the lower filter housing 310, distributes force as water flows through the filter assembly, thereby protecting the filter membrane 330 from rupture.

When the filter assembly 220 is connected to the pump tubing 120 and the water pump 130 is energized, a partial vacuum will form through the pump tubing 120 and within the filter assembly 220. At this point, when the induction tube 210 (or, alternatively, the narrow opening at the top of the upper filter housing 320 if the induction tube is not used) is submerged at least $1/16$ inch below the surface of the water being sampled a uniform seal between the water and the filter assembly 220 will be formed and the sampling process will commence. Liquid will enter into the upper filter housing 320 at a relatively low velocity and will continue to decrease in velocity until right before the filter membrane 330, at which point the pressure within the filter assembly 220 is at its highest. The purpose of this design is to allow heavier sediment to fall out of the filter assembly 220 rather than becoming imbedded in the filter membrane 330, which is made possible because the velocity of the liquid being filtered through the entry to the filter assembly 220 is lower than is required to attract or retain sediment, which is of a higher density than the surrounding fluid. This also allows for uniform usage of the filter membrane 330, which leads to more accurate water sampling results. After entering the filter assembly 220, the water first flows through the filter membrane 330, which will capture matter that cannot pass through, and then flows through the filter screen 340, at which time the pressure will begin to decrease as the velocity increases. Finally, the water will exit the filter assembly 220 through the lower filter housing 310 and continue to travel toward the water pump 130 to ultimately be discarded into the discharge container 190. After the target volume of liquid is filtered, the filter assembly 220 should be flipped upside down in an orientation relative to the sampling position in order to fully complete the sampling process. The pump should remain active until all water has passed through the filter membrane 330. After retracting the telescoping wand extension and enabling the biopod, the upper filter housing 320 should then be peeled away from the lower filter housing 310 using the pull tab on the upper filter housing 320. The filter membrane 330 will then be removed from the lower filter housing 310 for sample preservation or on-site analysis.

The seal that allows partial vacuum to form between the lower filter housing 310 and the upper filter housing 320 is created in two primary sections. The first sealing section is the point of contact between the lower filter housing 310 and the upper filter housing 320. The second, and more critical, sealing section is created by the interface between the outer annular bead on the lower filter housing 310 with the inwardly-extending flange on the upper filter housing 320, which is intended to snap under the annular bead. This is made possible by the selection of a stiff rubber-like material for the upper filter housing 320 and a hard polymer for the lower filter housing 310.

Figure 4:
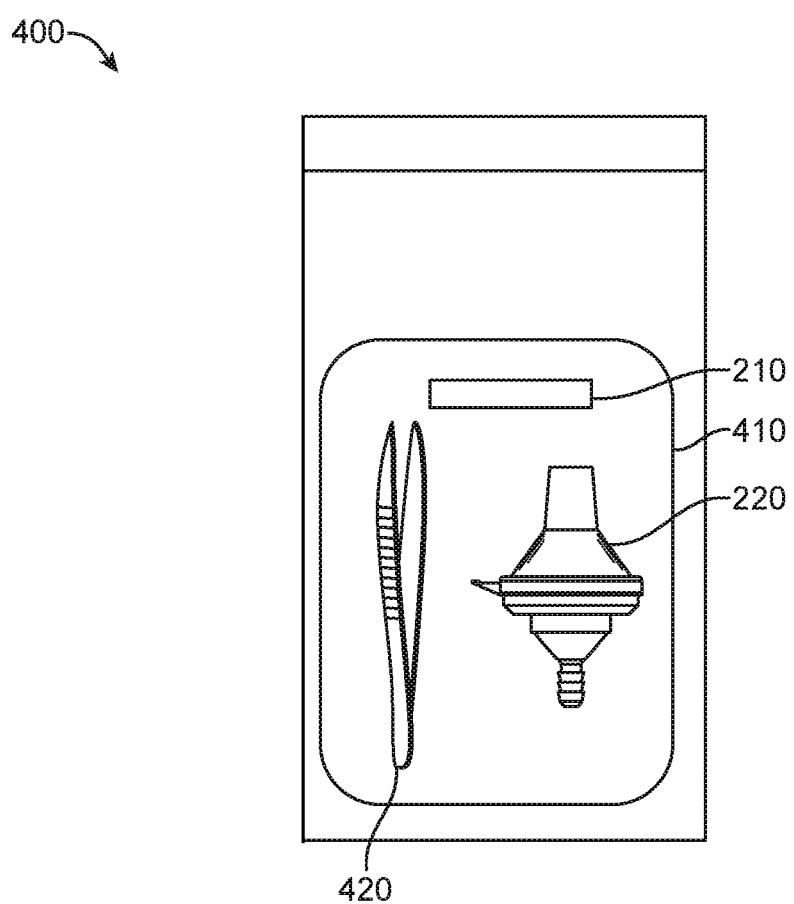
FIG. 4 is a front view diagram of the sample packet.

Now referring to FIG. 4 which depicts the inventive subject matter of the sample packet 400 comprising the sterile pouch 410, filter assembly 220, induction tube 210 and forceps 420. The sterile pouch 410 contains and provides protection from contamination of the filter assembly 220, induction tube 210, and the forceps 420 used to remove the filter membrane 330 from the filter assembly 220 subsequent to taking a water sample. The filter membrane 330 may contain a preservative, a lysis buffer, or a desiccant-filled pouch.

Figure 5:
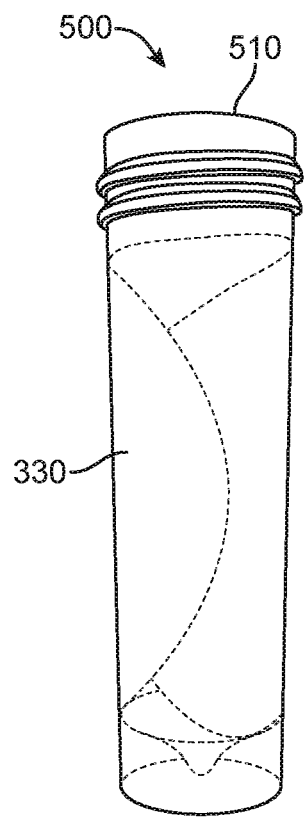
FIG. 5 is a side-view photograph of a storage container with filter membrane housed.

Now referring to FIG. 5 which depicts the inventive subject matter of the sample container 500 comprising the container tube 510 wherein the filter membrane 330 is stored subsequent to taking a water sample. The container tube 510 and filter membrane 330 are designed to be fitted with a container cap and stored for analysis of the collected particulate.

Figure 6:
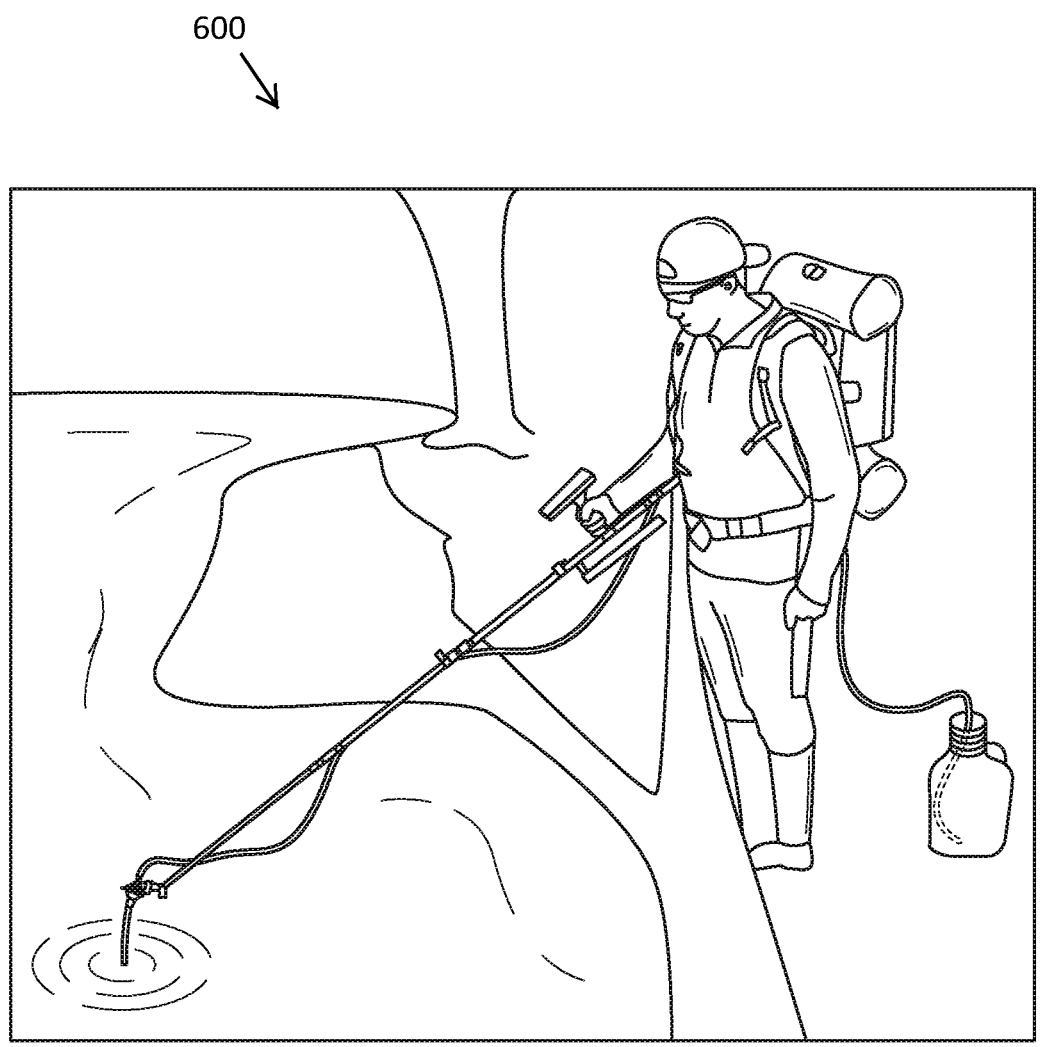
FIG. 6 is a side-view photograph of the dynamic environmental water sampling backpack being used in water sampling.
Figure 7:
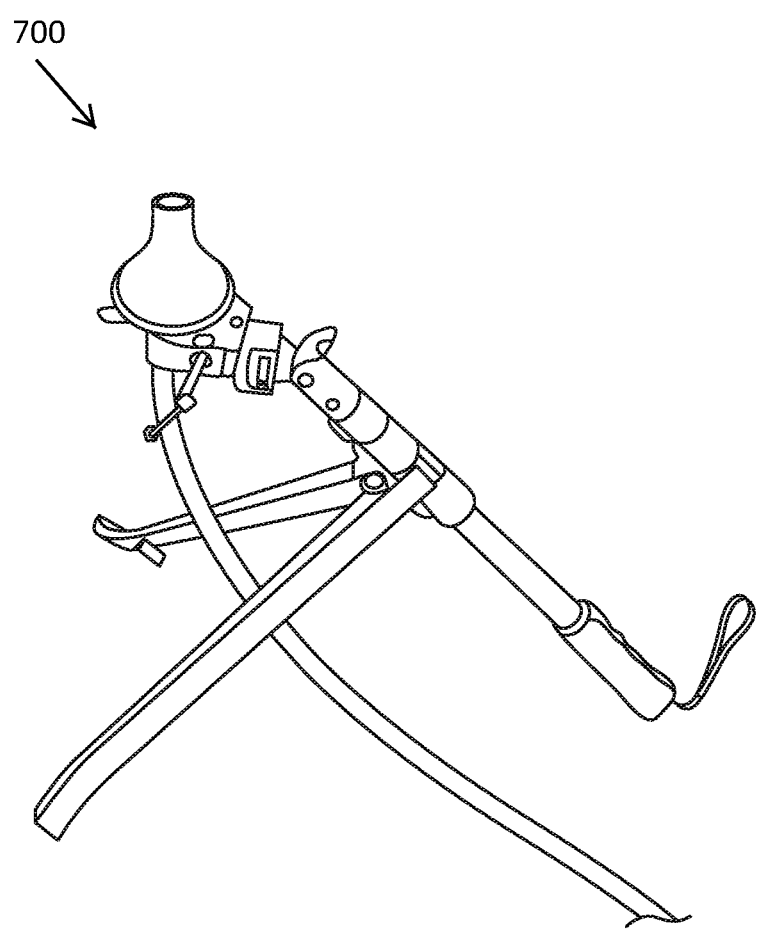
FIG. 7 is a side-view photograph of the filter assembly being drained subsequent to taking a water sampling.
Figure 8:
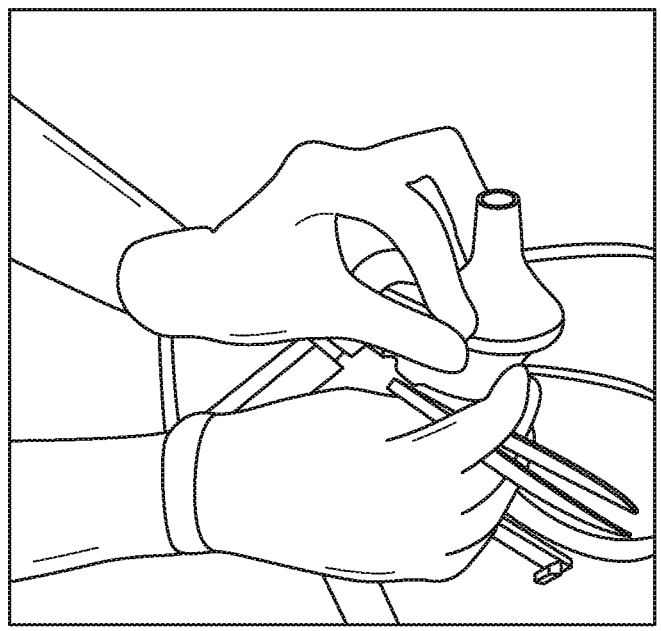
FIG. 8 is a side-view photograph of the removal of the upper filter housing from the lower filter housing subsequent to taking a water sampling.
Figure 9:
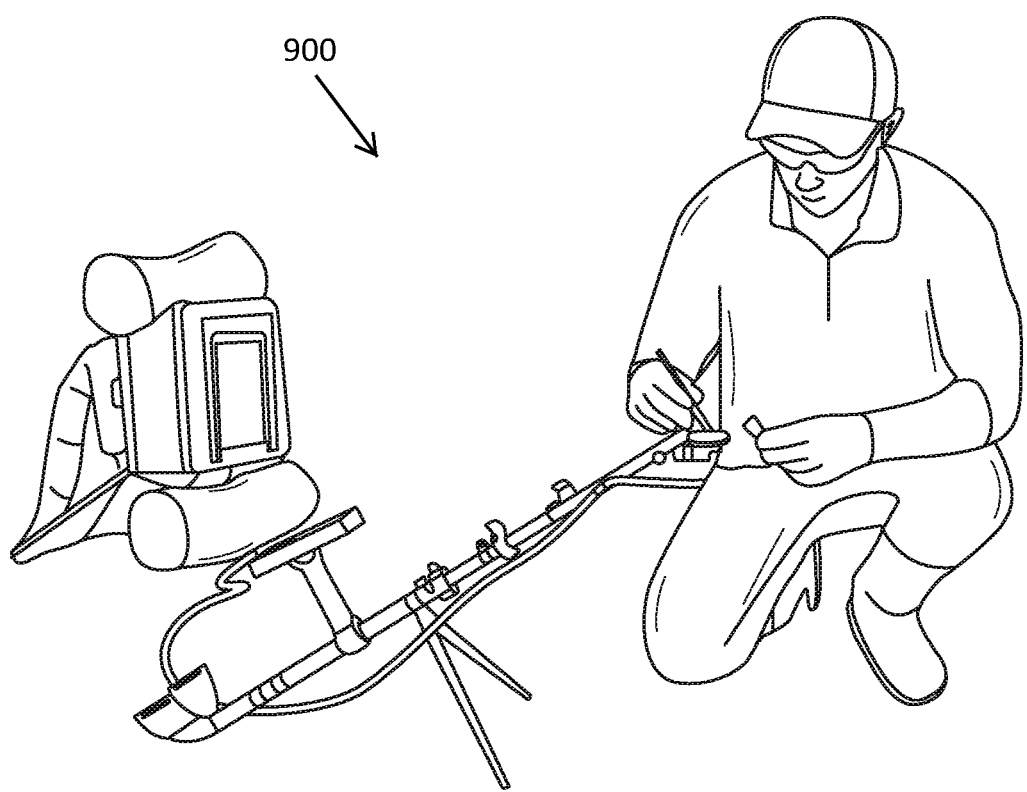
FIG. 9 is a side-view photograph of the removal of the filter membrane from the lower filter housing subsequent to taking a water sampling.
Figure 10:
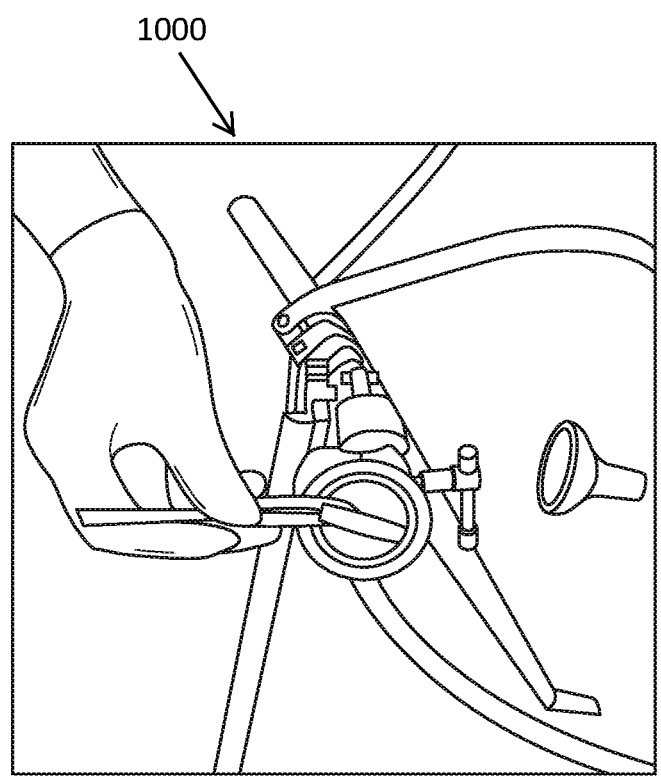
FIG. 10 is a top-view photograph of the removal of the filter membrane from the lower filter housing subsequent to taking a water sampling.

Now referring to FIG. 6-10 which depicts the inventive subject matter being used in the field. Specifically, FIG. 6 depicts the collection 600 of a sample from the water source, FIG. 7 depicts drainage 700 of the filter assembly subsequent to taking a water sample, FIG. 8 depicts the removal 800 of the upper filter housing from the lower filter housing, and FIGS. 9-10 depict the removal 900 and 1000 of the filter membrane from the inside of the lower filter housing.

In a preferred embodiment, an apparatus for a power and control of a water sampling system, includes a backpack-mounted device containing a controller casing, a protective lid, a storage compartment, a pump tubing, a positive displacement water pump, a pressure sensor, a pump system controller, a pump driver, an onboard computer, a user interface panel, a battery, a flow sensor and a discharge container, when the system is properly activated, water is drawn into and filtered through an induction and filtration apparatus, passed through the power and control apparatus and discharged into a discharge container and the feedback regarding flow rate and pressure is sent from one or more sensor devices to the pump system controller, and adjustments to the operating speed of the pump are automatically applied by the pump system controller through the pump driver based on the feedback to maintain a flow rate and a pressure of water being sampled within preset parameters input by a user. When activated in automated mode, the system will automatically alert the user and shut down when the preset parameter for maximum volume, input by the user, has been reached. The pressure sensor is an electric pressure sensor. The flow rate sensor detects the flow of water being sampled and relays the water flow rate to the remote flow controller. The user interface panel has a display screen, displaying water flow rate, pressure and volume metrics for a water sample.

In another preferred embodiment, an apparatus for the induction and filtration of water samples includes a sterile induction tube, said induction tube giving a user an option to separate a point of water sample intake from a point of water entry to a filter assembly, the filter assembly collecting particulate from water samples inducted into the apparatus, a pump tubing, the pump tubing directing the flow of water being sampled, a remote flow controller, the remote flow controller facilitating operation of a water pump in automatic or manual mode, displaying water volume on a display screen, and enabling positioning of a wand extension by use of a handle connecting the remote flow controller to the wand extension; and the wand extension providing rigidity support for the flow tube, flow rate sensor, filter assembly and wiring structure.

In yet another embodiment, a filter assembly for the collection of particulate from water samples includes a filter membrane wherein particulate can be extracted during a pass-through of a water sample, a filter screen wherein a force of the water passing through the filter assembly is distributed to preclude rupturing of the filter membrane, a lower filter housing and an upper filter housing wherein, when joined at their respective wide-end bases and the apparatus is properly assembled and operated, a water-tight and air-tight seal will be formed, such that the filter membrane will be protected from water-borne contaminants during sampling, such that a partial vacuum will form in the pump hose and the filter assembly, such that water entering the filter assembly will decrease in velocity and increase in pressure until it reaches the filter membrane; such that the heavier sediment present in the water sample will fall out of the filter assembly prior to reaching the filter membrane and such that the particulate captured by the filter membrane will not contain the heavier sediment.

In still yet another preferred embodiment, a method for an intake and filtration of a water sample, includes opening an air-tight sterile pouch, removing from the air-tight sterile pouch a sterile induction tube, a sterile filter assembly, and some sterile forceps, attaching a narrow-barbed opening of said filter assembly to an end of a pump tubing and, if conditions warrant an use of an intake extension, a narrow smooth end of the filter assembly to the intake tube, and inserting the filter assembly into a clip affixed to the support wand, activating an user interface panel and setting parameters for desired flow rate and pressure; and either setting a parameter for desired volume or overriding a volume parameter to operate in manual mode, inserting the intake portion of the system into a water source in order to commence the sampling process, monitoring water volume on a display screen attached to a remote pump control device wherein user controls can be input to override automatic mode if desired, tilting the system back following assembly at a conclusion of water intake in order to properly complete the sampling, such that residual sampled water passes completely through the filter assembly, removing from a sterile pouch a forceps and a sample container, opening the filter assembly, extracting the filter membrane using the forceps, and placing the filter membrane inside the sample container and storing the sample container in the storage compartment for subsequent analysis of the particulate captured therein.

Persons skilled in the art will recognize that many modifications and variations are possible in the details, materials, and arrangements of the parts and actions which have been described and illustrated in order to explain the nature of this inventive concept and that such modifications and variations do not depart from the spirit and scope of the teachings and claims contained therein.

All patent and non-patent literature cited herein is hereby incorporated by reference in its entirety for all purposes.

We claim:

1. A field research sampling system, comprising:
 a user worn backpack-mounted sampling system comprising:
  a backpack control module, the control module further comprising:
   a controller casing, a protective lid flexibly connected to the controller casing, a storage compartment proximately disposed within the controller casing; said storage compartment capable of receiving:
    preserved filter membranes, storage media for field data collection, pens or pencils for sample labeling and laboratory sample tubes or containers;
   a user interface panel having a display screen; the user interface panel further comprising the ability to enter setpoints for system parameters;
   an onboard computer operatively connected to a pump system controller; and
   a pump tubing having a first end and a second end; the first end of the pump tubing feeding through the controller casing and connected to a variable speed positive displacement water pump, an electric pressure sensor capable of measuring the water pressure in the pump tubing, a pump system controller able to modify the rate of water volume in the pump tubing, a pump driver;
   a power supply module, the power supply module electrically connected to the user interface panel, the onboard computer, the positive displacement pump, the electric pressure sensors, and the pump system controller;
 a water collection and filtration module comprising:
  an induction tube, a filter assembly, a remote flow controller, and a flow rate sensor operably coupled to the second end of the pumping tube, and operatively connected to the onboard computer and configured in a wand-like extension;
  the filter assembly further comprising:
   a funnel shaped upper filter housing, having a tapered-end and an open-end, the open-end of the upper filter housing able to support a filter membrane and a filter screen;
   a funnel shaped lower filter housing, having a tapered-end and an open-end, the open-end of the lower filter housing;
   the open-end of the upper filter housing sealably connected to the open end of the lower filter housing; and
   the induction tube operably coupled to the first end of a filter assembly, and the second end of the pump tubing coupled to the second end of the filter assembly
 so that a selectable rate of water is pumped into the sampling system as monitored by the flow rate sensor in operable regulation of water pressure by the pressure sensor yielding a collected sample on the filter membrane of a filter assembly of the filtration module and the flow rate of water is controlled by the onboard computer.

* * * * *